United States Patent [19]

Markezich

[11] 3,956,321

[45] May 11, 1976

[54] PREPARATION OF 4-FLUOROPHTHALIC ANHYDRIDE

[75] Inventor: Ronald L. Markezich, Scotia, N.Y.

[73] Assignee: General Electric Company, Schenectady, N.Y.

[22] Filed: Jan. 30, 1975

[21] Appl. No.: 545,480

[52] U.S. Cl. .............................................. 260/346.3
[51] Int. Cl.² ........................................ C07D 307/89
[58] Field of Search ................................. 260/346.3

[56] References Cited
OTHER PUBLICATIONS

Finger et al., J.A.C.S. Vol. 78, pp. 6034–6037 (1956).
Bartoli et al., J. of Chemical Society (Perkin I), p. 2671 (1972).
Gould, Mechanism and Structure in Organic Chemistry, New York – Holt, Rhinehart and Winston (1959) pp. 212–220.
Cram et al., Organic Chemistry, N. Y. – McGraw–Hill, (1959) pp. 311–312.
Pedersen, J.A.C.S. Vol. 89 (26), pp. 7017–7021 (1967).

*Primary Examiner*—Natalie Trousof
*Assistant Examiner*—Bernard Dentz
*Attorney, Agent, or Firm*—Joseph T. Cohen; Jerome C. Squillaro

[57] ABSTRACT

4-Fluorophthalic anhydride can be prepared by reacting potassium fluoride with 4-nitrophthalic anhydride. The use of solvents can increase the rate of reactivity and reduce the temperature at which reaction takes place. The more reactive 4-fluorophthalic anhydride can be used to make BPA-dianhydride employed in the production of polyetherimides.

1 Claim, No Drawings

PREPARATION OF 4-FLUOROPHTHALIC ANHYDRIDE

This invention is concerned with a process for making 4-fluorophthalic anhydride. More particularly the invention is concerned with a process for obtaining 4-fluorophthalic anhydride which comprises reacting 4-nitrophthalic anhydride with potassium flouride at elevated temperatures. Additional advantages can be derived by conducting the reaction in a suitable solvent, such as an aprotic solvent, for example, dimethyl sulfoxide, whereby shorter periods of time and lower temperatures can be employed for the reaction.

The compound 2,2-bis[4-(3,4-dicarboxyphenoxy)phenyl]propane dianhydride (hereinafter referred to as "BPA-dianhydride") and having the formula

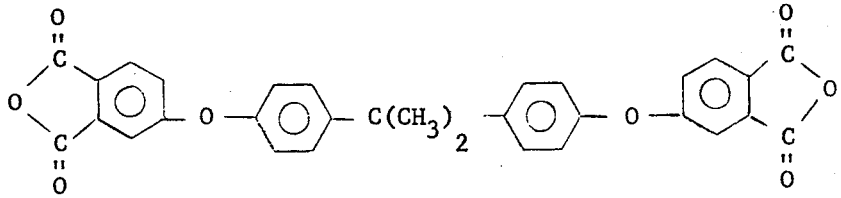

has been found to be useful in making polyetherimides by reacting the aforesaid BPA-dianhydride with an organic diamine such as methylene dianiline or oxydianiline to form a polymer corresponding to the general formula

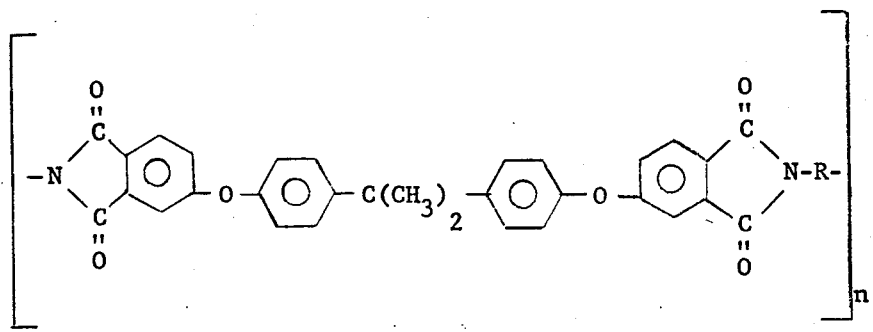

where R is a divalent organic radical, for example, phenylene, diphenylene oxide, etc. Such reactions are more particularly described in U.S. Pat. No. 3,847,867, issued Nov. 12, 1974, assigned to the same assignee as the present invention.

Generally, the BPA-dianhydride is made by effecting reaction between 4-nitrophthalimides and the dialkali metal salt of bisphenol A. There would be some advantages if instead of using the nitrophthalimides with the dialkali metal salt to make the BPA dianhydride through a complex processing technique, one could employ 4-fluorophthalic anhydride which is much more reactive with the dialkali metal salt of the bisphenol A. Past syntheses for making 4-fluorophthalic anhydride have involved such diverse methods as oxidation of 4-fluoro-o-xylene with nitric acid, the exchange of 4-chlorophthalic anhydride with potassium fluoride, and the preparation of the 4-fluorophthalic anhydride from 4-aminodiethylphthalate through the medium of the diazonium salt. Most of these syntheses are either complex or use starting materials that are not readily available.

Unexpectedly, I have discovered a simple method for making the 4-fluorophthalic anhydride by effecting reaction between 4-nitrophthalic anhydride and potassium fluoride. This reaction goes readily and efficiently and produces in good yields a product which requires little, if any, purification. It was entirely unexpected and in no way could have been predicted that the potassium fluoride would be so effective for reaction with the 4-nitrophthalic anhydride since attempts to use sodium fluoride in place of potassium fluoride produced no 4-fluorophthalic anhydride.

It was further unexpected to find that the potassium fluoride would react with the nitrophthalic anhydride since no reaction was detected between potassium fluoride and nitrobenzene. My above-described reaction was additionally unobvious despite the fact that it was known that potassium fluoride would react with nitro groups activated by strong electron withdrawing groups [e.g., see article entitled "Aromatic Fluorine Compounds. VII. Replacement of Aromatic —Cl and —NO₂ Groups by —F" by G. C. Finger and C. W. Kruse, JACS, 78, 6034 (1956) where activation was due to another nitro group, and an article by G. Bartoli

RD-7849 et al entitled "Fluorodenitration of Some Mildly Activated Nitro-compounds," Journal Chemical Society, Perkins I, page 2671, for 1972 where activation was due to a heterocyclic nitrogen in the form of a pyridine or a thiazole]. It is thus believed that the activating force for causing the nitro group on phthalic anhydride to react with the potassium fluoride comes from the anhydride group.

Generally, it is only necessary to heat at especially temperatures the 4-nitrophthalic anhydride with the potassium fluoride, advantageously in the anhydrous state. I have found that at least 1 mol of the potassium fluoride should be used per mol of the 4-nitrophthalic anhydride. The molar ratio can be varied widely and one can employ as much as 2 to 4 mols of the potassium fluoride per mol of the 4-nitrophthalic anhydride without departing from the scope of the invention. Generally, excess amounts of potassium fluoride are unnecessary, expecially since the potassium fluoride is rather expensive material.

The temperatures which can be employed in the practice of the present invention may be varied widely depending on whether a solvent is employed in the reaction mixture. Without any solvent, temperatures of the order of about 200° to 350°C. are normally used for times ranging from about 5 minutes to about one hour or more, the exact time being that required to give complete interchange between the potassium fluoride and the 4-nitrophthalic anhydride.

If a solvent is employed, the temperatures used can be considerably lower, and may range from about 75° to 200°C. for periods of time ranging from about 5 minutes to 30 minutes or more.

Among the aprotic solvents which may be employed in the practice of the present invention may be mentioned dimethyl sulfoxide, N-methyl pyrrolidone, N,N-dimethylformamide, N,N-dimethyl acetamide, etc. The amount of solvent used can also be varied widely. Since the 4-fluorophthalic anhydride is quite soluble in an aprotic solvent while the potassium fluoride is sparingly soluble, I have found that the amount of solvent can range, by weight, from about 0.2 to 8 parts or more of the solvent per part of the 4-nitrophthalic anhydride.

In order that those skilled in the art may better understand how the present invention may be practiced, the following examples are given by way of illustration and not by way of limitation.

EXAMPLE 1

Into a reaction vessel were placed 9.944 grams (0.052 mol) 4-nitrophthalic anhydride and 6.618 grams (0.114 mol) anhydrous potassium fluoride. The reaction vessel was closed and the reactants mixed together for several seconds; thereafter the reaction vessel was fitted with a distilling head, receiver, and nitrogen inlet. The reaction mixture was heated under a nitrogen blanket at approximately an increase of 2°/minute until the temperature reached 225°C. (which took about 45 minutes). The reaction mixture was then heated at a temperature of 235°–240°C. for an additional 60 minutes at which time the nitrogen line was replaced by a vacuum line and the pressure lowered until distillation of the reaction mixture began to take place. This resulted in a yield of 5.101 grams (59.6% yield) of 4-fluorophthalic anhydride, boiling point 205°–206°C./160 mm. This material, which on cooling solidified to give a solid melting at 74°–76°C., was identified as essentially pure 4-fluorophthalic anhydride.

EXAMPLE 2

Into a reaction vessel were placed 290 grams (1.5 mol) 4-nitrophthalic anhydride and 91 grams (1.57 mol) of anhydrous potassium fluoride. The reaction vessel was closed and shaken to mix the reactants and was then attached to a distilling head, receiver, and nitrogen inlet. The mixture was heated, under a nitrogen blanket beginning at 100°C. while the temperature was raised to 230°C. over a 25 minute period and kept at a temperature of 230°–250°C. for about 4 hours. After 2 hours, the nitrogen line was replaced by a vacuum line and the system evacuated to about 160 mm. This resulted in the collection over the next 2 hours of 148.5 grams (60% yield) 4-fluorophthalic anhydride, which upon analysis indicated the material to be greater than 97% pure (melting point 72°–76°C.).

EXAMPLE 3

To a reaction vessel fitted with a reflux condenser magnetic stirrer and nitrogen inlet were placed 3.35 grams (0.0174 mol) 4-nitrophthalic anhydride, 2.83 grams (0.036 mol) anhydrous potassium fluoride, and 8 ml. dry dimethyl sulfoxide. The reaction vessel was placed in an oil bath at 142°C. and kept at this temperature for about 35 minutes while stirring the reaction mixture. VPC analysis of a portion of the reaction mixture showed that the reaction was complete after about 20 minutes. The reaction mixture was cooled to room temperature and then poured into dilute aqueous hydrochloric acid and extracted with ethyl acetate to give a product which upon distillation gave 1.007 grams (about 35% yield) of 4-fluorophthalic anhydride.

I have also found that in addition to using aprotic solvents such as dimethyl sulfoxide, one can employ other solvents of a non-aprotic nature such as mixture of acetonitrile and a crown ether, specifically, 2,3,11,12-dibenzo-1,4,7,10,13,16-hexaoxacyclooctadeca-2,11-diene also known as "dibenzo-18-crown-6."

EXAMPLE 4

To a reaction vessel equipped with a reflux condenser, nitrogen inlet and oil bath were introduced 2.008 grams (0.035 mol) anhydrous potassium fluoride, 0.458 gram (0.0013 mol) dibenzo-18-crown-6, and 20 ml. dry acetonitrile. This mixture was refluxed at about 82°C. for 30 minutes, and thereafter 3.011 grams (0.016 mol) 4-nitrophthalic anhydride was added and the mixture refluxed for an additional 43 hours. After cooling to room temperature, methylene chloride was added to the reaction mixture, and the latter filtered to remove solid material. Concentration of the filtrate under vacuum yielded 2 grams of 4-fluorophthalic anhydride containing a small amount of the dibenzo-18-crown-6. To remove this latter crown ether, the material was dissolved in aqueous potassium hydroxide, extracted with ethyl acetate, and acidified with hydrochloric acid to a pH 1. Extraction with ethyl acetate yield 1.195 grams (42% yield) of pure 4-fluorophthalic acid which can be dehydrated to yield 4-fluorophthalic anhydride.

The polyetherimides obtained from the dianhydrides derived from the reaction of the dialkali metal salt of bisphenol A with the 4-fluorophthalic anhydride have excellent physical, chemical, and electrical properties. These polymers have many uses, for instance, in molding powder formulations either alone or mixed with other polymers and other fillers to make molded parts such as helical or beveled gears, ratchets, gaskets, valve seats, etc. They can also be used to prepare molded calendered, extruded articles, films, coatings, threads, filaments, tapes and the like for use in electrical applications such as cables, terminals, terminal blocks, and as components of dynamoelectric machines operated at elevated temperatures.

What I claim as new and desire to secure by Letters Patent of the United States is:

1. The process for making 4-fluorophthalic anhydride which comprises reacting 4-nitrophthalic anhydride with potassium fluoride at a temperature of from 75° to 200° C. in a solvent consisting essentially of acetonitrile and a crown ether.

* * * * *